US008444030B1

(12) United States Patent
Hanley

(10) Patent No.: US 8,444,030 B1
(45) Date of Patent: May 21, 2013

(54) TAMPON HOLSTER SYSTEM

(76) Inventor: Jeffrey A. Hanley, Tampa, FL (US)

( * ) Notice: Subject to any disclaimer, the term of this patent is extended or adjusted under 35 U.S.C. 154(b) by 544 days.

(21) Appl. No.: 12/660,273

(22) Filed: Feb. 24, 2010

Related U.S. Application Data

(60) Provisional application No. 61/212,233, filed on Apr. 9, 2009.

(51) Int. Cl.
*A61B 19/02* (2006.01)
*A61F 13/20* (2006.01)

(52) U.S. Cl.
USPC ............ 224/251; 224/673; 224/222; 224/267

(58) Field of Classification Search
USPC ........ 224/219, 222, 251, 267, 673; D3/203.5; 220/4.21, 4.24, 8; 206/270
See application file for complete search history.

(56) References Cited

U.S. PATENT DOCUMENTS

| | | | | |
|---|---|---|---|---|
| 1,532,614 A * | 4/1925 | Waibel | ........................... | 224/577 |
| 2,343,679 A * | 3/1944 | Lermer | ........................... | 224/222 |
| D156,948 S * | 1/1950 | Fisher | ........................... | D3/203.5 |
| 2,784,512 A * | 3/1957 | Goodwin | ........................... | 428/8 |
| 4,744,461 A * | 5/1988 | Lapham | ........................... | 206/5 |
| 4,964,526 A * | 10/1990 | Stephens | ........................... | 220/520 |
| 5,277,315 A * | 1/1994 | Plein | ........................... | 206/270 |
| 5,526,924 A * | 6/1996 | Klutznick | ........................... | 206/5 |
| 5,564,583 A * | 10/1996 | Kelley et al. | ............... | 220/23.83 |
| D408,626 S * | 4/1999 | Lage | ........................... | D3/203.5 |
| 6,298,857 B1 * | 10/2001 | Schmidt | ........................... | 131/250 |
| 6,382,407 B1 * | 5/2002 | Chao | ........................... | 206/5 |
| 7,017,744 B2 * | 3/2006 | Persson | ........................... | 206/440 |
| 7,390,590 B2 * | 6/2008 | Wani et al. | ........................... | 429/96 |

* cited by examiner

*Primary Examiner* — Nathan J Newhouse
*Assistant Examiner* — John Cogill

(57) ABSTRACT

An outer case has a lower portion with front, rear and side faces. The side faces couple the front and rear faces. The lower portion terminates in an open lower end and an upper end. The outer case has an upper portion terminating in a closed upper end. The outer case has a lower end. An inner case has front, rear, and side faces. The side faces couple the front and rear faces. The upper portion terminates in an open upper end and a lower end. The inner case has a lower portion terminating in a closed lower end and an upper end. A pair of parallel slots is formed in the rear face of the inner case. The slots are at a central elevational extent of the rear face of the inner case.

1 Claim, 2 Drawing Sheets

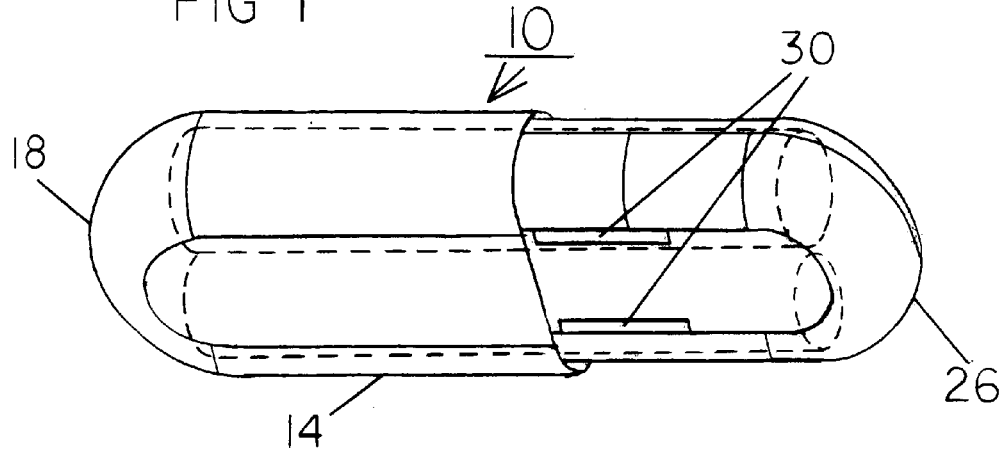
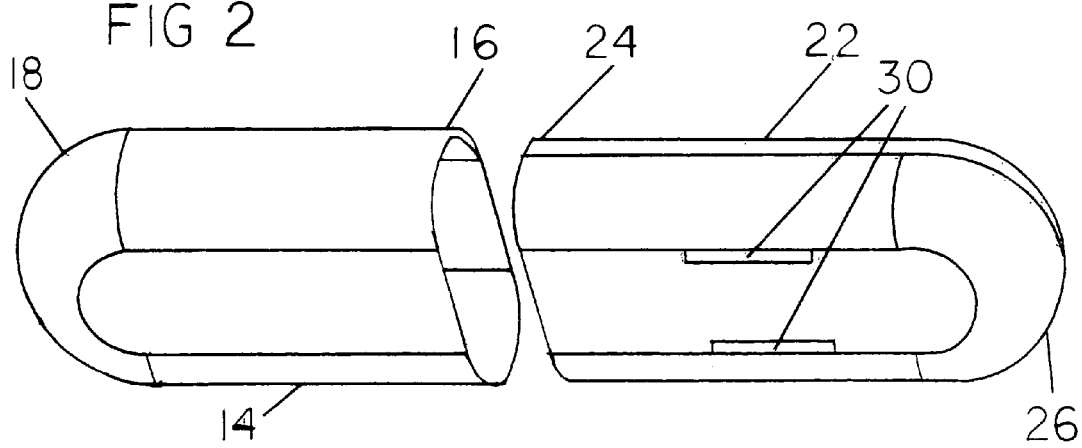

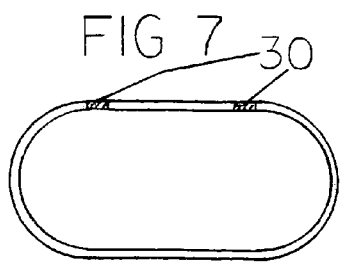
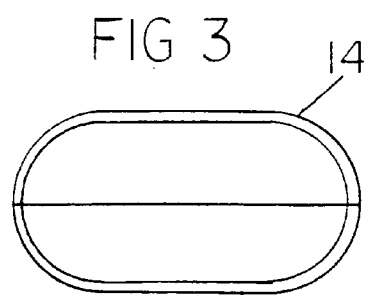
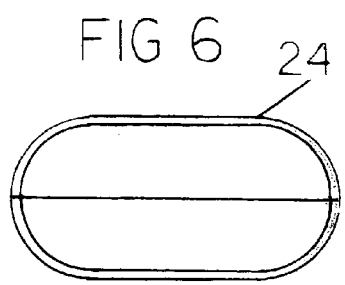
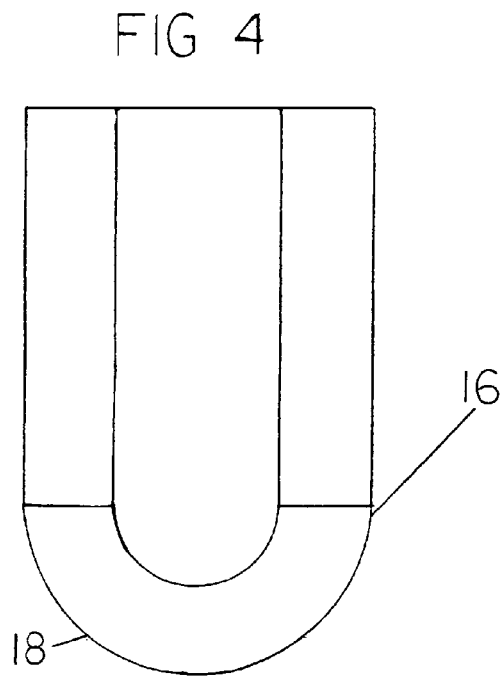
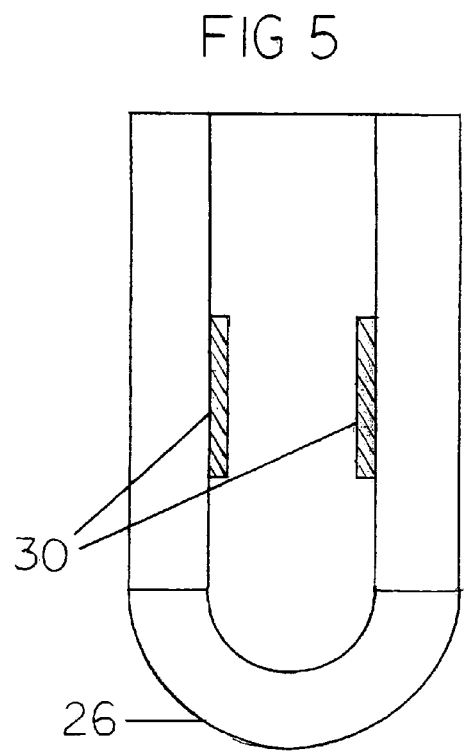

TAMPON HOLSTER SYSTEM

This application is based upon and claims the benefit of U.S. Provisional Application Ser. No. 61/212,233 filed Apr. 9, 2009, the subject matter of which is incorporated herein by reference.

BACKGROUND OF THE INVENTION

Field of the Invention

The present invention relates to a tampon holster system and more particularly pertains to removably supporting two tampons at a convenient location on the person of a female user in potential need of one of the tampons during an emergency situation, the supporting being done in a safe, convenient, discreet and economical manner.

SUMMARY OF THE INVENTION

In view of the foregoing disadvantages inherent in the types of feminine hygiene product holders of known designs and configurations now present in the prior art, the present invention provides an improved tampon holster system. As such, the general purpose of the present invention, which will be described subsequently in greater detail, is to provide a new and improved tampon holster system and method which has all the advantages of the prior art and none of the disadvantages.

To attain this, the present invention essentially comprises a tampon holster system. First provided is an outer case. The outer case has a lower portion. The lower portion is in a generally cylindrical configuration. The lower portion has a planar front face. The lower portion has a parallel planar rear face. The lower portion has curved side faces. The side faces couple the front and rear faces. The lower portion terminates in an open lower end below. The lower portion terminates in an upper end above. The outer case has an upper portion. The upper portion is in a curved configuration. The upper portion terminates in a closed upper end above. The upper portion terminates in a lower end below. The upper portion is integrally formed with the upper end of the lower portion of the outer case. The outer case is fabricated of an essentially rigid plastic material. The outer case has an interior surface. The outer case has an exterior surface. In this manner a common wall thickness is defined between the interior and exterior surfaces throughout the entire extent of the outer case.

An inner case is provided. The inner case has an upper portion. The upper portion is in a generally cylindrical configuration. The upper portion has a planar front face. The upper portion has a parallel planar rear face. The upper portion has curved side faces. The side faces couple the front and rear faces. The upper portion terminates in an open upper end above and a lower end below. The inner case has a lower portion. The lower portion is in a curved configuration. The lower portion terminates in a closed lower end below and an upper end above. The lower portion is integrally formed with the lower end of the upper portion of the inner case. The inner case is fabricated of an essentially rigid plastic material. The inner case has an interior surface. The inner case has an exterior surface. In this manner a common wall thickness is defined between the interior and exterior surfaces throughout the entire extent of the inner case.

Provided next are two tampons. The tampons have lower ends. The lower ends are removably received within the inner case. The tampons have upper ends. The upper ends extend above the inner case. The inner case is adapted to be slidably received by the outer case. In this manner the upper ends of the tampons are covered. The outer case is adapted to be separated from the inner case. In this manner the tampons are exposed. Further in this manner the tampons may be removed from the inner case and used.

Provided last is a pair of parallel slots. The slots are formed in the rear face of the inner case. The slots are provided in a central extent of the rear face adjacent to the side faces. The slots are adapted to receive and slidably retain a securement strap. The securement strap is not shown. In this manner the inner and outer cases and tampons may be positioned on an appendage of a user, such as an arm or a leg, at a discreet location. The strap, when utilized, is adapted to limit the extent of sliding of the outer case with respect to the inner case and tampons. In this manner the inadvertent crushing of tampons in the inner case is abated.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tampon holster system which has all of the advantages of the prior art feminine hygiene product holders of known designs and configurations and none of the disadvantages.

It is another object of the present invention to provide a new and improved tampon holster system which may be easily and efficiently manufactured and marketed.

It is a further object of the present invention to provide a new and improved tampon holster system which is of durable and reliable constructions.

An even further object of the present invention is to provide a new and improved tampon holster system which is susceptible of a low cost of manufacture with regard to both materials and labor, and which accordingly is then susceptible of low prices of sale to the consuming public, thereby making such tampon holster system economically available to the buying public.

Even still another object of the present invention is to provide a tampon holster system for removably supporting two tampons at a convenient location on the person of a female user in potential need of one of the tampons during an emergency situation, the supporting being done in a safe, convenient, discreet and economical manner.

Lastly, it is an object of the present invention to provide a new and improved tampon holster system. An outer case has a lower portion with front, rear and side faces. The side faces couple the front and rear faces. The lower portion terminates in an open lower end and an upper end. The outer case has an upper portion terminating in a closed upper end. The outer case has a lower end. An inner case has front, rear, and side faces. The side faces couple the front and rear faces. The upper portion terminates in an open upper end and a lower end. The inner case has a lower portion terminating in a closed lower end and an upper end. A pair of parallel slots is formed in the rear face of the inner case. The slots are at a central elevational extent of the rear face of the inner case.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of a tampon holster system constructed in accordance with the principles of the present invention.

FIG. 2 is an exploded perspective illustration of the system shown in FIG. 1.

FIG. 3 is a plan view and

FIG. 4 is a front elevational view of the outer case shown in FIGS. 1 and 2.

FIG. 5 is a plan view and

FIG. 6 is a front elevational view of the outer case shown in FIGS. 1 and 2 and FIG. 7 is a cross sectional view through the center of the inner case.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved tampon holster system embodying the principles and concepts of the present invention and generally designated by the reference numeral 10 will be described.

The present invention, the tampon holster system 10 is comprised of a plurality of components. Such components in their broadest context include an outer case, an inner case, and a pair of parallel slots. Such components are individually configured and correlated with respect to each other so as to attain the desired objective.

First provided is an outer case (14). The outer case has a lower portion (16). The lower portion is in a generally cylindrical configuration. The lower portion has a planar front face. The lower portion has a parallel planar rear face. The lower portion has curved side faces. The side faces couple the front and rear faces. The lower portion terminates in an open lower end below. The lower portion terminates in an upper end above. The outer case has an upper portion (18). The upper portion is in a curved configuration. The upper portion terminates in a closed upper end above. The upper portion terminates in a lower end below. The upper portion is integrally formed with the upper end of the lower portion of the outer case. The outer case is fabricated of an essentially rigid plastic material. The outer case has an interior surface. The outer case has an exterior surface. In this manner a common wall thickness is defined between the interior and exterior surfaces throughout the entire extent of the outer case.

An inner case (22) is provided. The inner case has an upper portion (24). The upper portion is in a generally cylindrical configuration. The upper portion has a planar front face. The upper portion has a parallel planar rear face. The upper portion has curved side faces. The side faces couple the front and rear faces. The upper portion terminates in an open upper end above and a lower end below. The inner case has a lower portion (26). The lower portion is in a curved configuration. The lower portion terminates in a closed lower end below and an upper end above. The lower portion is integrally formed with the lower end of the upper portion of the inner case. The inner case is fabricated of an essentially rigid plastic material. The inner case has an interior surface. The inner case has an exterior surface. In this manner a common wall thickness is defined between the interior and exterior surfaces throughout the entire extent of the inner case.

Provided next are two tampons. The tampons have lower ends. The lower ends are removably received within the inner case. The tampons have upper ends. The upper ends extend above the inner case. The inner case is adapted to be slidably received by the outer case. In this manner the upper ends of the tampons are covered. The outer case is adapted to be separated from the inner case. In this manner the tampons are exposed. Further in this manner the tampons may be removed from the inner case and used.

Provided last is a pair of parallel slots (30). The slots are formed in the rear face of the inner case. The slots are provided in a central extent of the rear face adjacent to the side faces. The slots are adapted to receive and slidably retain a securement strap. The securement strap is not shown. In this manner the inner and outer cases and tampons may be positioned on an appendage of a user, such as an arm or a leg, at a discreet location. The strap, when utilized, is adapted to limit the extent of sliding of the outer case with respect to the inner case and tampons. In this manner the inadvertent crushing of tampons in the inner case is abated.

In the preferred embodiment, the inner case has a total length of 3.250 inches with a 0.825 inch radius of curvature at its closed end. It has a depth of 8.20 inches with a 0.410 inch radius of curvature at its sides. The outer case has a total length of 2.900 inches with a 0.870 inch radius of curvature at its closed end. It has a depth of 0.910 inches with a 0.455 inch radius of curvature at its sides. Both cases have a 0.040 inch thickness.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A tampon holster system (10) for removably supporting two tampons at a convenient location on the person of a female user in potential need of one of the tampons during an emergency situation, the system comprising, in combination:

an outer case (14) having a lower portion (16) in a generally cylindrical configuration with a planar front face and a parallel planer rear face and semicircular side faces coupling the front and rear faces, the lower portion terminating in an open lower end below and an upper end above, the outer case having an upper portion (18) in a semicircular configuration terminating in a closed upper end above and a lower end below integrally formed with the upper end of the lower portion of the outer case, the outer case being fabricated of an essentially rigid plastic material with an interior surface and an exterior surface defining a common wall thickness between the interior and exterior surfaces throughout the entire extent of the outer case;

an inner case (22) having an upper portion (24) in a generally cylindrical configuration with a planar front face and a parallel planar rear face and semicircular side faces coupling the front and rear faces, the upper portion terminating in an open upper end above and a lower end below, the inner case having a lower portion (26) in a semicircular configuration terminating in a closed lower end below and an upper end above integrally formed with the lower end of the upper portion of the inner case, the inner case being fabricated of an essentially rigid plastic material with an interior surface and an exterior surface defining a common wall thickness between the interior and exterior surfaces throughout the entire extent of the inner case;

two tampons having lower ends removably received within the inner case, the tampons having upper ends extending above the inner case, the inner case adapted to be slidably received by the outer case to cover the upper ends of the tampons, the outer case adapted to be separated from the inner case to expose the tampons for removal from the inner case and use; and a pair of parallel slots (30) formed in the rear face of the inner case, the slots extending through a central extent of the rear face adjacent to the side faces, the slots adapted to receive and slidably retain a securement strap for positioning the inner and outer cases and tampons on an appendage of a user at a discreet location, the strap when utilized adapted to limit the extent of sliding of the outer case with respect to the inner case and tampons and thereby abate inadvertent crushing of tampons in the inner case.

* * * * *